US007875582B2

(12) United States Patent
Pham et al.

(10) Patent No.: US 7,875,582 B2
(45) Date of Patent: *Jan. 25, 2011

(54) NONBAR PERSONAL PRODUCT COMPOSITIONS COMPRISING CRYSTALLINE WAX STRUCTURED BENEFIT AGENT PREMIX OR DELIVERY VEHICLE

(75) Inventors: Quynh Pham, Murray Hill, NJ (US); Stephen M. O'Connor, New York, NY (US); John R. Glynn, Jr., Westfield, NJ (US); Alexander Lips, Edgewater, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 78 days.

This patent is subject to a terminal disclaimer.

(21) Appl. No.: 10/443,569

(22) Filed: May 22, 2003

(65) Prior Publication Data
US 2004/0235691 A1 Nov. 25, 2004

(51) Int. Cl.
*A61K 7/50* (2006.01)
(52) U.S. Cl. ........................ 510/141; 510/152; 510/153; 510/155
(58) Field of Classification Search ................ 510/130, 510/426, 463; 424/70.1
See application file for complete search history.

(56) References Cited
U.S. PATENT DOCUMENTS

| 5,437,859 | A | 8/1995 | Ser et al. |
| 5,661,189 | A | 8/1997 | Grieveson et al. |
| 5,674,511 | A | 10/1997 | Kacher et al. |
| 5,804,540 | A * | 9/1998 | Tsaur et al. ................ 510/135 |
| 5,817,609 | A | 10/1998 | He et al. |
| 6,080,708 | A * | 6/2000 | Glenn et al. ................ 510/130 |
| 6,645,511 | B2 | 11/2003 | Aronson et al. |
| 6,673,755 | B2 * | 1/2004 | Wei et al. .................... 510/130 |
| 6,716,440 | B2 | 4/2004 | Aronson et al. |
| 2003/0049282 | A1 | 3/2003 | Aronson et al. |
| 2003/0054019 | A1 | 3/2003 | Aronson et al. |
| 2003/0082222 | A1 | 5/2003 | Miyamoto |
| 2003/0171231 | A1* | 9/2003 | Shana'a et al. ............. 510/130 |

FOREIGN PATENT DOCUMENTS

| EP | 0 294893 | 12/1988 |
| EP | 0 413417 A2 | 2/1991 |

(Continued)

OTHER PUBLICATIONS

European Search Report Application No. EP 04 25 2715 dated Sep. 13, 2004.

(Continued)

*Primary Examiner*—Necholus Ogden, Jr.
(74) *Attorney, Agent, or Firm*—Ronald A. Koatz

(57) ABSTRACT

The present invention relates to compositions comprising a structured benefit agent pre-mix or delivery vehicle comprising benefit agent structured with crystalline materials, as defined, which, when separately prepared and combined after preparation, provides enhanced delivery of benefit agent from a carrying composition into which the premix is added. The use of structured benefit agent also enhances delivery of separate benefit agents in the premix (which may or may not be structured) and of separate benefit agents added separately from the premix.

9 Claims, 4 Drawing Sheets

FOREIGN PATENT DOCUMENTS

Figure 1:
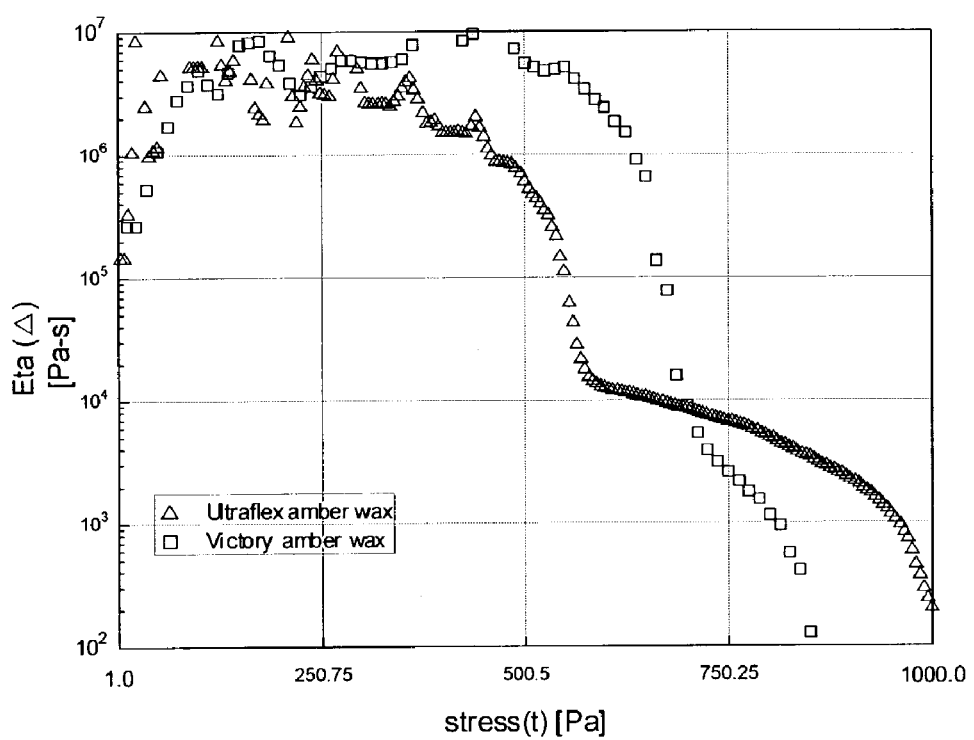

WO 02/39974 A1 5/2002
WO 03/074020 A1 9/2003

OTHER PUBLICATIONS

Brief Communication dated Aug. 7, 2009 with attached correspondence (in German) from Beiersdorf.

Document D11—labeled Comparative tests for Beiersdorf; this is English translation of correspondence attached to Aug. 7, 2009 Brief Communication.

Translation of opposition in related J6843 case (10 pages).

D1 reference dated Jul. 21, 2009 (3 pages).

* cited by examiner

NONBAR PERSONAL PRODUCT COMPOSITIONS COMPRISING CRYSTALLINE WAX STRUCTURED BENEFIT AGENT PREMIX OR DELIVERY VEHICLE

FIELD OF THE INVENTION

The present invention comprises a structured premix or "delivery vehicle" composition designed to enhance delivery (e.g., via enhanced deposition) of hydrophobic benefit agent(s), for example, moisturizing oils, from non-bar personal product compositions (e.g., liquid soap, creams, emulsions, etc.). When the structured benefit agent composition is separately prepared and combined with the personal product composition (preferably, while structured, the premix composition is still in a molten or liquid state although it can also be semi-molten or solid), a non-bar personal product composition is provided which yields enhanced delivery of the benefit agent(s).

It should be noted that not only the benefit agent which is structured will benefit from enhanced delivery, but also benefit agents which are separately found in the composition (e.g., entrapped within a network formed by the structured benefit agent or added separately and not as part of the premix) also may have enhanced delivery. The separate, not necessarily independently structured benefit agent (and certainly not structured as defined in the invention if not added with the premix) may be other hydrophobic benefit agents (e.g., perfumes, shine enhancing benefit agents, emollients) or hydrophilic benefit agents (e.g., glycerol).

BACKGROUND

Hydrophobic benefit agents (e.g., oils) can provide moisturizing and/or conditioning benefits to the skin or to hair. At present, however, it is extremely difficult to achieve high levels of deposition from personal product compositions, particularly wash-off liquid products, such as personal wash liquid cleansers.

While this and co-pending applications are described with skin cleansing to personal product language, to the extent the structured benefit agents can be used in a variety of other compositions where deposition of benefit agents is desirable (e.g., hair, deodorant), the claims are intended to be read expansively and limited only by the structuring component.

Specifically, applicants have now unexpectedly found that use of certain "structured" benefit agents (e.g., oils and other hydrophobic benefit agents) act as so-called delivery vehicles for the benefit agent(s) which they are structuring leading to multiple benefits relative to benefit agents which are delivered without the specific structuring of the invention; or to other benefit agents used in final compositions where no other structured benefit agents are used. According to the invention, preferably the benefit agent being structured and the structuring material (e.g., crystalline wax) are separate components.

By specifically selecting particular crystalline structurant or structurants (i.e., so that the crystals have specifically defined aspect ratios), and by separately preparing structured benefit agent as a premix in the manner described (i.e., separate preparation and incorporation into product in a molten, or semi-molten or solid state), the benefit agent structurant vehicle (i.e., structured benefit agent vehicle) provides enhanced deposition as well as desired in-use and after-use sensory attributes (e.g., smooth skin feel).

As noted, such structured benefit agent also helps deposition of other benefit agents whether used in the same pre-mix (it is not clear whether they are separately structured or trapped in a network, but result is same), or whether separately added with other composition components.

Specifically, the invention relates to the use of hydrophobic benefit agent or agents structured by crystalline structurant or structurants selected from the group consisting of natural and synthetic crystalline structuring materials (e.g., waxes) wherein, when the structured benefit vehicle is separately prepared before combining with the non-bar personal product composition, the final composition is provided with benefit agent deposition to substrate of at least 5% greater, preferably at least 10% greater and often far greater than the level of deposition obtained if the benefit agent was added without being structured or without being in the presence of a structured benefit agent in the final formulation. In one embodiment, the benefit agent is oil and the structured benefit agent provides deposition greater than about 60 µg/cm$^2$ (measured in accordance with the protocol detailed in the examples). Unlike prior art references where deposition is dependent on the large size of the benefit agent droplets (e.g., >50 micrometers average droplet diameter), the deposition results of the subject invention have no requirement of large droplet size and are not dependent on size. The structured benefit agent also provides enhanced deposition of hydrophobic or hydrophilic benefit agents separately added.

Among the natural crystalline waxes which may be used as benefit agent(s) structurant are included petroleum derived waxes such as paraffins and microcrystalline waxes; as well as animal and plant (vegetable) waxes. Among the synthetic crystalline waxes which may be used are crystalline polymers such as polyethylene.

Some prior art references purport to use rheological parameters to select oils or oil blends to be used for improving deposition or providing favorable sensory feel.

U.S. Pat. No. 5,674,511 to Kacher et al., for example, describes the use of solubility parameters and four rheological parameters to select benefit agents (i.e., oil or oil blends) that can be used in moisturizing cleansing formulations to improve deposition and provide favorable sensory feels. Petrotum and petrolatum-containing mixtures are said to be favorable selections. The reference fails to teach or suggest the building of a deformable network of crystals within the benefit agent, and which crystals must have a specific aspect ratio. The Kacher reference fails to teach or suggest that the structured benefit agent can be combined with other components in the compositions in a molten, semi-molten or solid state. Also, it does not describe separate benefit agent and structurant, as is preferred by the subject invention (i.e., in the subject invention, if petrolatum is used, it is preferably used as a structurant to structure other benefit agents rather than itself comprise the structured benefit agent). In short, the benefit agents (e.g., oils) of Kacher clearly do not appear to be internally structured delivery vehicles like those used in the compositions of the invention which are separately prepared and wherein structurant has a defined aspect ratio.

A number of prior art references disclose generally the concept of an oil additive which can thicken or stabilize oils. They do not, however teach or disclose that specific crystalline structurant (i.e., having a defined aspect ratio), when prepared in combination with a hydrophobic benefit agent as a premix/delivery vehicle (added in molten, semi-molten or solid state; and combined with a carrying composition) will enhance deposition (by an amount of at least 5%) and/or will provide enhanced sensory benefits. Moreover, in contrast to these references where deposition is disclosed as a function of large droplet size of the benefit agent, in the subject invention deposition will occur independent of such large droplet size requirement.

U.S. Pat. No. 5,804,540 to Tsaur et al. and U.S. Pat. No. 5,661,189 to Grieveson, for example, disclose use of both crystalline or micro-crystalline waxes and hydrophobic polymers to thicken low viscosity oil so as to control the oil droplet size (i.e., it must attain a certain minimum size to deposit) as well as to maintain high lather. As noted above, however, there is no discussion of the criticality of crystalline structure (aspect ratio) or that a thickened benefit agent must be separately prepared and added in a molten or semi-molten state. Further, as noted, there is no recognition that it is critical the thickener must be a natural or synthetic crystalline structuring material (as is the case with subject invention) or that deposition occurs without the need for large droplet size. Indeed, the preferred thickening materials claimed in these patents provide only a very modest enhancement of deposition of low viscosity oils when they are incorporated into our invention.

In co-pending U.S. patent application Ser. No. 09/859,862 to Aronson et al. (entitled "Wet-Skin Treatment Composition"), filed May 17, 2001 and 09/859,849 to Aronson et al. (entitled "Method of Enhanced Moisture or Reduced Drying Using Wet-Skin Treatment Compositions"), there is disclosed benefit agents which provide a draggy feel. There is no teaching or disclosure however, of using benefit agent structurant with crystalline materials of specific aspect ratio or of how to produce such.

No prior art of which applicants are aware demonstrates the use of natural or synthetic crystalline structurants (e.g., wax) having specific aspect ratio of crystals and prepared as a premix to enhance the deposition of benefit agents (e.g., skin nutrients such as, for example, sunflower seed oil).

BRIEF DESCRIPTION OF THE INVENTION

Accordingly, the present invention relates to non-bar personal wash or personal product compositions (including liquid soap, creams, emulsions and also including hair, deo or any other compositions where enhanced benefit agent delivery is desirable), preferably liquid compositions comprising structured benefit agent composition for delivering a benefit agent(s) (e.g., oil) wherein said composition comprises:

(1) 0 to 99%, preferably 1 to 75%, more preferably 3 to 70% by wt. surfactant; and (2) 0.1 to 90% of a benefit agent delivery vehicle (structured benefit agent) wherein:

(a) 0.1 to 99.9, preferably 0.5 to 99.5, more preferably 1 to 99% by wt. of the structured delivery vehicle comprises one or more benefit agents or mixtures thereof; and (b) 99.9 to 0.1%, preferably 99.5 to 0.5% by wt. of the structured delivery vehicle comprises a crystalline structurant or structurants selected from the group consisting of natural and synthetic materials (e.g., waxes). Among natural crystalline waxes is included petroleum derived waxes (paraffin, microcrystalline waxes), animal waxes and plant waxes. Among synthetic crystalline waxes is included crystalline polymers such as, for example, polyethylene and synthetic derivatives of natural waxes;

wherein crystals of the crystalline structurant (e.g. wax) have an aspect or axial ratio such that length A to width B of the crystals has a ratio A/B>1, The length is to be understood as the longer of the two dimensions when considering both length and width.

When said premix (structured benefit agent composition) is separately prepared and properly combined with a carrying composition (i.e., surfactant containing or non-surfactant containing non-bar personal product composition), in which the structured benefit agent will be used to deliver the benefit agent to the substrate, said composition will have benefit agent deposition of greater than about 5%, preferably greater than 10% relative to level of deposition from the final composition if the benefit agent had not been structured, or if the benefit agent had not been in the presence of a structured benefit agent. In one embodiment, the benefit agent is oil and deposition is greater than about 60 $\mu g/cm^2$. The structured benefit agent premix should preferably be sufficiently pourable so that it can be added to the carrying composition which is why, generally, it will be in molten or semi-molten state. However, it should be understood that, even if not pourable, it can still be added. The deposition of the benefit agent is not dependent on large droplet size (i.e., can be small or large drops).

The use of structured benefit agent also enhances delivery of benefit agent(s) in the premix which may not be independently structured (e.g., may be caught in a network) or which may be added separately and not as part of the premix.

As noted, the structured benefit agent or delivery vehicle of this invention may be used in non-bar, preferably liquid, personal product compositions (including hair and deo, for example). The composition will typically comprise (a) 0 to 99%, preferably 1 to 75% of a surfactant system comprising a surfactant or surfactants selected from the group consisting of anionic, nonionic, amphoteric/zwitterionic, cationic surfactants and mixtures thereof and (b) 0.1 to 90%, preferably 0.5 to 80%, even more preferably 1-40% by weight of the structured benefit agent delivery vehicle as defined above.

In another aspect of the invention, the invention comprises a process for forming non-bar, preferably liquid, personal product composition comprising the delivery vehicle noted above which process comprises:

(1) mixing hydrophobic benefit agent or agents and crystalline structurant at processing conditions (e.g., a temperature sufficiently high) so that a premix of the benefit agent and structurant and preferably, though not necessarily, will be flowable and will pour (e.g., having viscosity of less than 250 Pa-s, more preferably less than 200 Pa-s, most preferably less than 100 Pa-s);

(2) combining said separately prepared premix and the carrying composition, preferably with stirring;

(3) if necessary, because the mixture had been heated, cooling the resulting mixture to room temperature.

In another embodiment, the invention provides a method for enhancing deposition of benefit agent, and providing smooth skin feel which method comprises applying a personal product cleanser comprising:

(a) 0 to 99% surfactant; and (b) 0.1 to 90% of benefit agent delivery vehicle wherein:

(i) 0.1 to 99.9% by wt. structured benefit agent vehicle comprises one or more benefit agents or mixtures thereof; and (ii) 99.9 to 0.1% by wt. of structured benefit agent vehicle comprises a crystalline structurant wherein the structurant is selected as noted above.

BRIEF DESCRIPTION OF THE DRAWINGS

FIG. 1 is a yield stress plot of a structured benefit agent composition comprising sunflower seed oil structured with a wax (Ultraflex amber or Victory amber) of the invention. Ultraflex amber wax and Victory amber wax were each mixed with sunflower seed oil at a ratio of wax/oil of 1:4. The graph shows how the structured benefit agent yields under high stress, a property specific to the structured benefit agents of the invention. At low stresses the viscosity of the structured benefit agent composition, (measured in Pascal seconds, or Pa-s) is essentially constant. As the applied stress is increased and reaches the yield stress value, the viscosity drops sharply and the material flows more readily.

Figure 2:
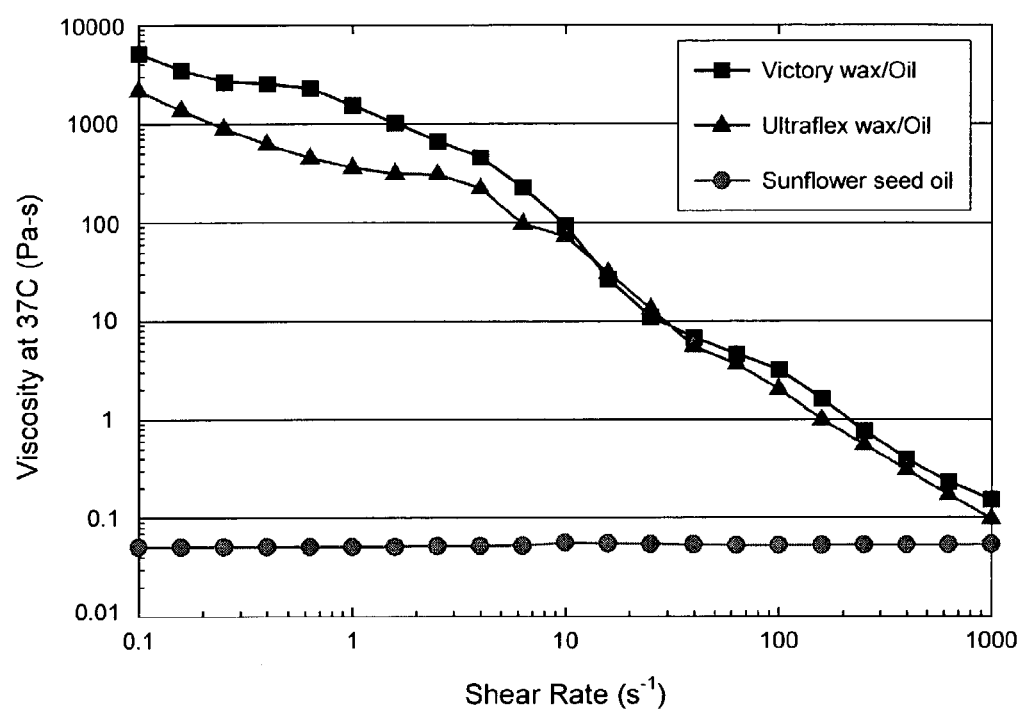

FIG. 2 is a plot showing shear thinning behavior of structured benefit agents of the invention versus an unstructured benefit agent. Ultraflex amber wax and Victory amber wax were each mixed with sunflower seed oil at a ratio of wax/oil of 1:4. For comparison, the viscosity behavior with shear of unstructured sunflower seed oil is also shown. Plotted is viscosity versus shear rate. At low shear rates the viscosity of structured benefit agents, sunflower seed oil structured with wax (Ultraflex amber wax or Victory amber wax) is very high. As the applied shear rate is increased the viscosity of the structured benefit agents decreases and continues to decrease at the higher shear rates. At sufficiently high shear rates the viscosity of structured benefit agents approaches that of the pure unstructured benefit agent component.

FIGS. 3a and 3b are schematics of typical crystal structurants of the invention having length "A" and width "B". As noted, the aspect or axial ratio of A/B must be greater than 1. The length is to be understood as the longer of the two dimensions when considering length and width.

Figure 4:
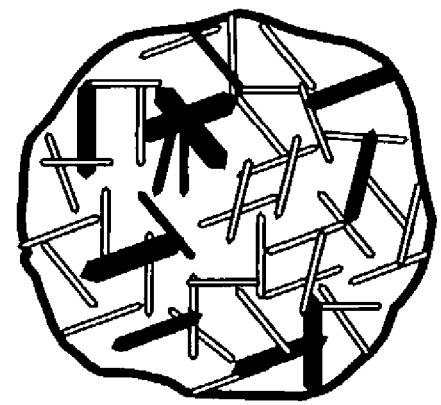

FIG. 4 is a schematic of structurant crystals (which can be "plate-like") forming a three-dimensional network within the structured benefit agent (e.g., oil).

DETAILED DESCRIPTION OF THE INVENTION

The present invention relates to a non-bar, preferably liquid, personal product composition (as noted, this may include any composition which incorporates a benefit agent desirably deposited including, but not limited to, hair and deodorant compositions) comprising a structured benefit agent delivery vehicle composition which, because of the structure of the crystal used to prepare it (for example, aspect ratio of the crystalline structurants), and, because of its manner of preparation (separately prepared) forms a structured benefit agent component which has particular properties (e.g., yield stress, shear thinning) which permit the structured benefit agent component or components to deposit more efficiently from the composition onto skin or other substrate. Further, use of the structured benefit agents permits enhanced deposition of other benefit agents in the premix (whether entrapped or independently added) as well as those in the composition that are separately added.

Yield stress parameters can be 1-5000 Pa or higher and all ranges subsumed therein (see FIG. 1) and shear thinning parameters can range from 2000 Pa-s (or higher) at low shear rates (0.1/sec) (i.e., viscosity of 1000 to 10,000 Pa-s as seen on the Y axis of FIG. 2) to 0.1 Pa-s (or lower) at high shear rates (100/sec) (again, see FIG. 2). Both yield stress and shear-thinning parameters/ranges are dependent on the level of benefit agent structurant added to benefit agent.

When specific crystalline materials are used to structure the structured benefit agent, and when the process of the invention is used, a final composition containing the structured benefit agent vehicle will deliver hydrophobic benefit agent to the skin or substrate at an exceedingly efficient level, i.e., at least 5% greater than if not used. Moreover, such deposition is not dependent on large droplet size of the structured benefit agent droplets in the carrying composition (e.g., liquid soaps). It also may enhance deposition of other benefit agent(s), whether in the premix or separately added.

The "structured" benefit agent (e.g., oil) of the subject invention can be envisioned as an emollient droplet which has certain physical properties defining at least in part the ability of the structured benefit agent to deliver the benefit agent more efficiently from the final composition.

More specifically, when crystalline waxes structure the benefit agent, the crystals in the benefit agent phase are believed to create a solid network which is apparently interconnected like a "house of cards" for plate-like crystals or perhaps more like a scaffold structure when the crystalline structurant has rod/needle morphology. The crystals form a three-dimensional supporting network that, without wishing to be bound by theory, is believed to make the wax structured benefit agents, for example, more than just thickened benefit agents (see FIG. 4). The crystalline structure changes the normally fluid benefit agent (e.g., vegetable or other oils) into solid-like materials that have good flow and spreading properties for benefit agent deposition. Through selection of structurant (e.g., wax) and calculation of structurant content, the structured benefit agent can be tailored to meet desired Theological parameters. An important part of the invention is that the crystal forming this 3-D network must have an aspect or axial ratio of length and width (A and B, respectively) such that A/B>1. This aspect ratio of the crystals is believed to enhance deposition of the structured benefit agent (see FIG. 3). The length is to be understood as the longer of the two dimensions when considering both length and width.

The structured benefit agents of the invention have been found to deposit much better from the non-bar cleansers than if the benefit agent is not structured. Again, while not wishing to be bound by theory, deposition is believed to occur by direct transfer where the affinity of the structured benefit agent for surfaces is related to the properties of the crystals (e.g., aspect ratio) used to structure.

The structured benefit agent can be seen as a premix since it is a critical aspect of the invention that the benefit agent being structured and the crystalline structurant forming the "structure" be combined before adding to the carrying composition in which the structured benefit agent will be used. In this sense, the premix or structured benefit agent is acting as a vehicle for delivery of the benefit agent. On the other hand, the structured benefit agent may also enhance deposition of other benefit agents either by entrapping these benefit agents in a network formed by the structured benefit agent (if other benefit agent is in premix for example) or even if the other benefit agent is separately added to the composition separate from the premix.

The structured benefit agent vehicle specifically comprises:

(a) 0.1 to 99.5%, preferably 0.5 to 99.5% by wt. (including all ranges subsumed therein) of the vehicle comprising one or more benefit agents or mixtures thereof; and (b) 99.9 to 0.1, preferably 99.5 to 0.5% by wt. (including all ranges subsumed therein) of the vehicle comprising a crystalline structurant selected from the group consisting of natural and synthetic crystalline materials (e.g., waxes).

Benefit Agent

The benefit agent of the subject invention may be a single benefit agent component. Further the benefit agent may be a mixture of two or more components, one or all of which may have a beneficial aspect.

As noted, a separate benefit agent may also have enhanced deposition, even if it is not clear this is due to structuring or because it is entrapped in a network. Further, the structured benefit agent may enhance deposition of a benefit agent which is separately added (see, for example, applicants' co-pending application which is hereby incorporated by reference relating to enhanced hydrophilic benefit agent deposition).

The benefit agents can be emollients, moisturizers, anti-aging agents, anti-inflammatory agents, skin-toning agents, skin lightening agents, sun screens, fragrances, etc.

The preferred list of benefit agents include:
(a) silicone oils, gums and modifications thereof such as linear and cyclic polydimethylsiloxanes; amino, alkyl alkylaryl and aryl silicone oils;
(b) fats and oils including natural fats and oils such as jojoba, soybean, sunflower seed oil, rice bran, avocado, almond, olive, sesame, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;
(c) waxes such as carnauba, spermaceti, beeswax, lanolin and derivatives thereof;
(d) hydrophobic plant extracts;
(e) hydrocarbons such as liquid paraffins, petrolatum, vaseline, microcrystalline wax, ceresin, squalene, pristan, paraffin wax and mineral oil;
(f) higher fatty acids such as behenic, oleic, linoleic, linolenic, lanolic, isostearic and poly unsaturated fatty acids (PUFA);
(g) higher alcohols such as lauryl, cetyl, stearyl, oleyl, behenyl, cholesterol and 2-hexydecanol alcohol;
(h) esters such as cetyl octanoate, myristyl lactate, cetyl lactate, isopropyl myristate, myristyl myristate, isopropyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;
(i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;
(j) lipids such as cholesterol, ceramides, sucrose esters and pseudo-ceramides as described in European Patent Specification No. 556,957;
(k) vitamins such as vitamin A and E, and vitamin alkyl esters, including those vitamin C alkyl esters;
(l) sunscreens such as octyl methoxyl cinnamate (Parsol MCX) octocrylene(2-ethylhexyl 2-cyano-3,3-diphenylacrylate), octyl salicylate (2 ethylhexyl salicylate), benzophenone-3 (2-hydroxy-4-methoxy benzophenone), and avobenzone (4-tert-butyl-4'-methoxydibenzoylmethane) (these are merely illustrative);
(m) phospholipids;
(n) particles having a wide range of shapes, surface characteristics, and hardness characteristics which can be utilized to provide optical effect. Water-insoluble particles can be derived from a wide variety of materials including those derived from inorganic, organic, natural, and synthetic sources. Non-limiting examples of these materials include those selected from the group consisting of almond meal, alumina, aluminum oxide, titanium dioxide, mica, coated mica, sodium stearate, stearic acid, zinc stearate, aluminum silicate, apricot seed powder, attapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e., polytetrafluoroethylene), polyhalogenated olefins, pumice rice bran, rye flour, sericite, silica, silk sodium bicarbonate, sodium silicoaluminate, soy flour synthetic hectorite, talc, tin oxide, titanium dioxide, tricalcium phosphate, walnut shell powder, wheat bran, wheat flour, wheat starch, zirconium silicate, and mixtures thereof. Also useful are micronized particles made from mixed polymers (e.g., copolymers, terpolymers, etc.), such as polyethylene/polypropylene copolymer, polyethylene/propylene/isobutylene copolymer, polyethylene/styrene copolymer, and the like; and
(o) anti-aging, wrinkle-reducing, skin whitening, anti-acne, and sebum reduction agents such as alpha-hydroxy acids and esters, beta-hydroxy acids and ester, polyhydroxy acids and esters, kojic acid and esters, ferulic acid and ferulate derivatives, vanillic acid and esters, dioic acids (such as sebacid and azoleic acids) and esters, retinol, retinal, retinyl esters, hydroquinone, t-butyl hydroquinone, mulberry extract, licorice extract, and resorcinol derivatives;
(p) fragrance molecules which include acetanisol; amyl acetate; anisic aldehyde; anisole; anisylalcohol; benzaldehyde; benzyl acetate; benzyl acetone; benzyl alcohol; benzyl formate; hexenol; laevo-carveol; d-carvone; cinnamaldehyde; cinnamic alcohol; cinnamyl acetate; cinnamyl formate; cis-3-hexenyl acetate; Cyclal C (2,4-dimethyl-3-cyclohexen-1-carbaldehyde);
dihydroxyindole; dimethyl benzyl carbinol; ethyl acetate; ethyl acetoacetate; ethyl butanoate; ethyl butyrate; ethyl vanillin; tricyclo decenyl propionate; furfural; hexanal; hexenol; hydratropic alcohol; hydroxycitronellal; indole; isoamyl alcohol; isopulegyl acetate; isoquinoline; ligustral; linalool oxide; methyl acetophenone; methyl amyl ketone; methyl anthranilate; methyl benzoate; methyl benzyl acetate; methyl heptenone; methyl heptyl ketone; methyl phenyl carbinyl acetate; methyl salicylate; octalactone; para-cresol; para-methoxy acetophenone; para-methyl acetophenone; phenethylalcohol; phenoxy ethanol; phenyl acetaldehyde; phenyl ethyl acetate; phenyl ethyl alcohol; prenyl acetate; propyl butyrate; safrole; vanillin; viridine, allyl caproate, allyl heptoate, anisole, camphene, carvacrol, carvone, citral, citronellal, citronellol, citronellyl acetate, citronellyl nitrile, coumarin, cyclohexyl ethylacetate, p-cymene, decanal, dihydromyrcenol, dihydromyrcenyl acetate, dimethyl octanol, ethyllinalool, ethylhexyl ketone, eucalyptol, fenchyl acetate, geraniol, gernyl formate, hexenyl isobutyrate, hexyl acetate, hexyl neopentanoate, heptanal, isobornyl acetate, isoeugenol, isomenthone, isononyl acetate, isononyl alcohol, isomenthol, isopulegol, limonene, linalool, linalyl acetate, menthyl acetate, methyl chavicol, methyl octyl acetaldehyde, myrcene, napthalene, nerol, neral, nonanal, 2-nonanone, nonyl acetate, octanol, octanal, α-pinene, β-pinene, rose oxide, α-terpinene, γ-terpinene, α-terpinenol, terpinolene, terpinyl acetate, tetrahydrolinalool, tetrahydromyrcenol, undecenal, veratrol, verdox, allyl cyclohexane propionate, ambrettolide, Ambrox DL (dodecahydro-3a,6,6,9a-tetramethyl-naphtho[2,1-b]furan), amyl benzoate, amyl cinnamate, amyl cinnamic aldehyde, amyl salicylate, anethol, aurantiol, benzophenone, benzyl butyrate, benzyl iso-valerate, benzyl salicylate, cadinene, campylcyclohexal, cedrol, cedryl acetate, cinnamyl cinnamate, citronellyl isobutyrate, citronellyl propionate, cuminic aldehyde, cyclohexylsalicylate, cyclamen aldehyde, dihydro isojamonate, diphenyl methane, diphenyl oxide, dodecanal, dodecalactone, ethylene brassylate, ethylmethyl phenylglycidate, ethyl undecylenate, exaltolide, Galoxilide™ (1,3,4,6,7,8-hexhydro,4,6,6,7,8,8-hexamethyl-cyclopenta-γ-2-benzopyran), geranyl acetate, geranyl isobutyrate, hexadecanolide, hexenyl salicylate, hexyl cinnamic aldehyde, hexyl salicylate, α-ionone, β-ionone, γ-ionone, α-irone, isobutyl benzoate, isobutyl quinoline, Iso E Super™ (7-acettl, 1,2,3,4,5,6,7,8-octahydro,1,1,6,7-tetramethyl napthalene), cis-jasmone, lilial, linalyl benzoate, 20methoxy naphthaline, methyl cinnamate, methyl eugenol, γ-methylionone, methyl linolate, methyl linolenate, musk indanone, musk ketone, musk tibetine, myristicin, neryl acetate, δ-nonalactone, γ-nonalactone, patchouli alcohol, phantolide, phenylethyl benzoate, phenylethylphenylacetate, phenyl heptanol, phenyl hexanol, α-santalol, thibetolide, tonalid, δ-undecalactone, γ-undecalactone, vertenex, vetiveryl acetate, yara-yara, ylangene; and (q) mixtures of any of the foregoing benefit agents.

To the extent materials above are hydrophobic, they are delivered as part of the premix (and more probably, although not necessarily, are structured; that is, at least one hydrophobic benefit agent will be structured, but others may be entrapped in the benefit agent network). Although not listed above, hydrophilic benefit agents may also be entrapped in the structured benefit agent network of the premix or separately added outside the premix. This is discussed, for example, in applicants' copending application relating to hydrophilic benefit agents hereby incorporated by reference into the subject application.

Natural or Synthetic Crystalline Structurant

The crystalline structurant used for "structuring" the benefit agent oil or emollient of the subject invention may be a natural or synthetic crystalline wax. Mineral, animal or plant (vegetable) waxes are all described as natural waxes. Synthetic waxes are described as those waxes that have been synthetically polymerized from raw materials or chemically modified natural waxes.

Among the natural crystalline waxes which may be used are petroleum based waxes such as paraffins and microcrystalline wax. Chemically, both microcrystalline (MC) and paraffin waxes are very similar, consisting of long saturated hydrocarbon chains. Both types of waxes are separated from crude petroleum with the MC waxes typically having higher molecular weights. Paraffin wax is extracted from the high boiling fractions of crude petroleum during the refining process by cooling and filtering. Following a sweating process to remove remaining oil in the wax, the resulting paraffin wax typically has less than 0.5% oil. There are many different grades available mostly varying in melting point. Generally, paraffin waxes are colorless or white and transparent. Paraffin waxes consist mainly of straight chain molecules with a small amount of branched-chain molecules mostly having branching near the end of the chains. As a result of the long, straight chains, paraffin wax has large, well-formed crystals. Molecular weights of paraffin waxes generally range from 360 to 420 (26 to 30 carbon atoms), although versions with longer chains (molecular weights up to 600) are available. Typical melting points are 126-134° F. (52-57° C.), the high molecular weight versions have melting points near 170° F. (77° C.). Paraffin waxes are brittle and the addition of oil weakens the structure (lowers the tensile strength).

Microcrystalline waxes (MC) differ from paraffin waxes in physical properties, chain structure and length, and in the process of manufacture. They are tougher, more flexible and have higher tensile strength and melting points than paraffin waxes. MC waxes have high affinity for oil which, when added, increases the wax plasticity. MC wax cannot be distilled without decomposition and therefore is separated from the residual distillation fraction of crude petroleum by dewaxing processes involving recrystallization in organic solvents and centrifugation. Oil content varies with grade but is usually around 2 to 12%. MC waxes contain mostly branched-chain molecules located at random along the chain with some straight chains. Typical melting points are 145 to 195° F. (63-91° C.). A high penetration number indicates flexibility of the wax, but flexibility is not a function of melting point.

There are also other mineral waxes such as montan wax, lignite wax, osocerite, ceresin, utah wax and peat wax.

Animal waxes can be obtained from such things as bees, insects or whales. These waxes include but are not limited to beeswax, Chinese wax, shellac wax, spermaceti and wool wax. Beeswax, for example, classified as an animal wax, is secreted by the honey bee to construct the honeycomb. The wax is harvested by melting the honeycomb and filtering away the wax. Beeswax has melting points around 61-65° C. and is compatible with almost all waxes and oils.

Plant waxes can be derived from beans, leaves and berries. Plant or vegetable waxes can include bayberry, candelilla, carnauba, cotton, esparto, fir, Japan, ouricury, palm, rice-oil, sugar cane, ucuhuba and cocoa butter.

Among synthetic crystalline waxes which may be used are crystalline polymers such as polyethylene, polymethylene, chemically modified waxes, polymerized alpha olefins and synthetic animal waxes. For example, siliconyl beeswax may be used which is beeswax that has been chemically modified.

A sample of various waxes which may be used according to the subject invention and of their properties is set forth below in Table 1.

TABLE 1

Waxes and their Properties

| Wax | Manufacturer | Classification* | Penetration No.** (25° C.) | Melting Point (° C.) |
| --- | --- | --- | --- | --- |
| Ultraflex Amber | Bareco Products | MC | 27 | 74.1 |
| Victory Amber | Bareco Products | MC | 28 | 79.1 |
| White Petrolatum | Penreco | MC | — | 54 |
| Multiwax ML-445 | Crompton Corp. | MC | 30 | 79.4 |

TABLE 1-continued

Waxes and their Properties

| Wax | Manufacturer | Classification* | Penetration No.** (25° C.) | Melting Point (° C.) |
|---|---|---|---|---|
| Multiwax 180-M | Crompton Corp. | MC | 18 | 85 |
| Multiwax W-835 | Crompton Corp. | MC | 70 | 76.7 |
| Multiwax X145A | Crompton Corp. | MC | 40 | 74 |
| Paraffin Wax 50/155 | Frank B. Ross Co., Inc. | P | 12 | 67 |
| Siliconyl Beeswax | Koster Kuenen, Inc. | DN | N/A | 70 |
| Be Square 175 white | Bareco Products | MC | 15 | 82.5 |
| Be Square 175 black | Bareco Products | MC | 18 | 82.3 |
| Perrowax 2250F | The International Group | MC | N/A | 40 |
| Beeswax NF | Frank B. Ross Co., Inc. | N | 18 | 62.5 |

*MC: microcrystalline; P: paraffin; N: natural/animal; dN: derivative of natural/animal wax
**Penetration No.: Penetration number values as reported by manufacturers using the standard test method for needle penetration of petroleum waxes of the American Society for Testing and Materials (ASTM D1321). The depth of penetration of needle in tenths of a millimeter (dmm) is measured with a penetrometer that applies a standard needle to the sample for 5 seconds under a load of 100 grams.

Another structuring material of the invention (e.g., used for structuring other benefit agents) is the microcrystalline wax petrolatum (also known as petrolatum or mineral jelly), which typically comprises about 90% by wt. of a natural mixture of microcrystalline waxes plus minor amounts of other impurities.

Structured Benefit Agent

As noted above, the wax in the benefit agent is believed to form a three-dimensional supporting network which is believed to make the structured benefit agent more than just thickened benefit agents. That is, it changes the consistency of the fluid benefit agent (e.g., oil) to a solid-like material having good spreading/deposition properties. Deposition is believed to occur by transfer of structured benefit agent droplets/particles to the substrate surface from the composition where the crystalline structure of the structuring material crystals (e.g., aspect ratio) is believed to help enhance affinity of the structured benefit agent to the substrate.

Other benefit agents in the premix may also structure (i.e., 2 or more) or just one may structure and/or the other benefit agent may have enhanced deposition by being entrapped in the network formed by the structured benefit agent.

The benefit agent may comprise 0.1 to 99.9% by wt. of the delivery vehicle/premix and structurant may comprise 99.9 to 1% by wt. of the delivery vehicle. Preferably benefit agent is 0.5 to 99.5%, more preferably 1 to 99% of vehicle. In some preferred embodiment, benefit agent comprises 50-99% of vehicle while wax is 1 to 50%, preferably 2 to 45% of benefit agent vehicle.

When used, for example, as part of a cleanser emulsion where structuring material (e.g., wax) is 20% of benefit agent phase, droplet diameters of the structured benefit agent may be in the range of 1-15 μm, with average droplets having a size of 4-8 μm. As noted, however, there is no requirement that droplets must be of this size.

When incorporated into liquid cleanser formulations, the structured benefit agent droplets are generally solid when stored at room temperature and may be seen as particles. The droplets may be somewhat spherical but have a rough, textured surface, a result of the structurant crystal within the drops As mentioned, there is no large size requirement for the structured benefit agent droplets of the invention. Unlike prior art, the structured benefit agent can deposit high benefit agent amounts even at small droplet sizes, i.e., below 10 μm and possibly even submicron.

As also mentioned, low levels (<50% of structured benefit agent) of structurant can be used.

Figure 3:
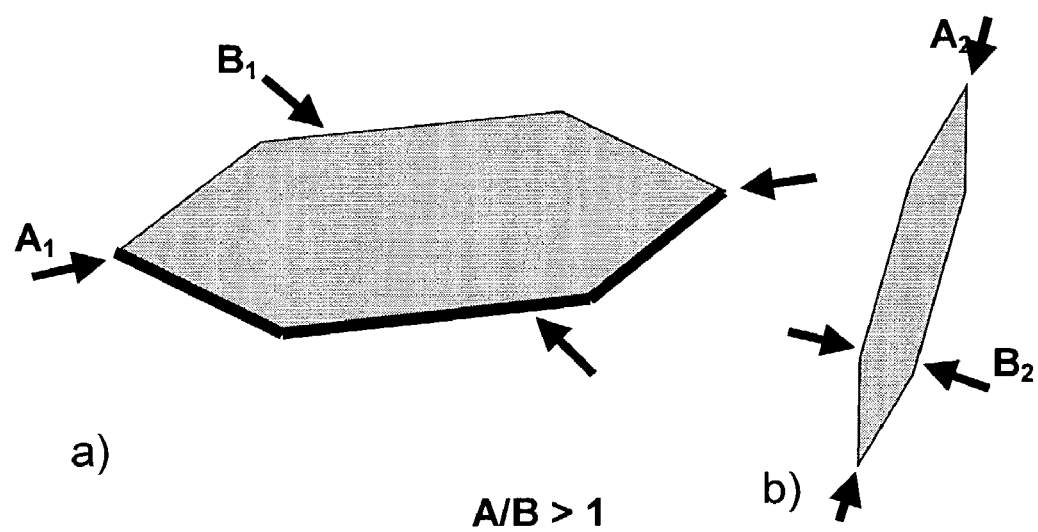

The only criticality is that the shape of the structurant have high axial or aspect ratio (A/B>1). This is shown in FIG. 3. The length is to be understood as the longer of the two dimensions when considering length and width. The fact that structuring exists is shown by high yield stress observed on benefit agents even when using low amount of structurant (see FIG. 1).

The structured benefit agent of the invention may also be used in combination with other materials that have been shown to enhance the deposition of hydrophobic benefit agents (e.g., cationic polymers, inorganic thickening agents such as clays or silicas, and polymer thickening agents).

Finally, as noted, the structured benefit agent may enhance deposition of other non-structured benefit agents which are not part of the premix. This phenomenon is described, for example in one of applicants co-filed, co-pending applications.

Process

A critical aspect of the subject invention is that the benefit agent (at least one) and crystalline structurant must be combined (e.g., in a premix) before they are combined with the carrying composition. The combination of such premix with carrying composition should preferably, although not necessarily, be when the structured benefit agent is in a molten or semi-molten state such that it can be poured into the carrying composition. That is, the viscosity of structured benefit agent premix when mixing should preferably be no higher than about 250 Pa-s, more preferably 200 Pa-s, most preferable 150 Pa-s.

In one embodiment of the invention, the crystalline structurant and benefit agent (e.g., an emollient oil such as sunflower seed oil) are combined and may be heated to a temperature above the melting point of the structurant. These are then preferably mixed to uniformity.

Preferably, the molten material is added to a carrying composition, preferably a surfactant containing carrying composition and maintained at the same temperature as the benefit agent and structurant mixture. After mixing (about 10 seconds to an hour, preferably 5 minutes to 45 minutes), the mixture is cooled, if necessary, to room temperature. As noted, structurant is combined with benefit agent before addition to the carrying composition (e.g., aqueous surfactant phase). It should be noted that a pourable viscosity may also be obtained by vigorous mixing of structurant and benefit agent and that heating is not necessarily required.

When such process is followed, the resulting structured benefit agent compositions will have the properties described above (i.e. shear thinning, yield stress etc.) and provide deposition of benefit agent, when measured from the carrying composition, of greater than about 5%, preferably greater than about 10% relative to level of deposition of benefit agent to substrate from final composition if the benefit agent had not been structured, or the benefit agent not being in the presence, in the final formulation, of a structured benefit agent. In one embodiment, the benefit agent is oil and deposition is at least about 60 µg/cm², preferably at least about 75, more preferably at least about 100 µg/cm².

As indicated above the structured benefit agent of the invention is used in non-bar, preferably liquid personal product compositions.

Liquid Compositions

In one embodiment of the invention, the premix comprising oil/benefit agent may be used in a liquid (e.g., personal wash cleanser) composition. Typically, such composition comprises as follows:
(1) 0% to 99%, preferably 1 to 75% by wt., more preferably 3 to 70% by wt. of a surfactant selected from the group consisting of anionic, amphoteric, nonionic and cationic surfactant and mixtures thereof;
(2) 0.1% to 90%, preferably 0.5% to 80% of a delivery vehicle comprising 0.1 to 99.9% delivery vehicle benefit agent or agents and 99.9 to 0.1% delivery vehicle crystalline structurant(s) selected from the group consisting of natural and synthetic crystalline waxes;
(3) optional ingredients for liquid personal cleanser; and
(4) balance water,
wherein the premix (structured benefit agent) is incorporated into liquid compositions as a separate premix; and
wherein deposition of oil/emollient from the liquid composition onto substrate is greater than about 5% greater than if the benefit agent were not structured or not in the presence of a structured benefit agent.

Surfactant System

Anionic Surfactants

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula $$R^4CONHCH_2CH_2O_2CCH_2CH(SO_3M)CO_2M$$

wherein $R^4$ ranges from $C_8$-$C_{22}$ alkyl and M is a solubilizing cation;

amido-MIPA sulfosuccinates of formula $$RCONH(CH_2)CH(CH_3)(SO_3M)CO_2M$$

where M is as defined above.

Also included are the alkoxylated citrate sulfosuccinates; and alkoxylated sulfosuccinates such as the following:

$$R-O-(CH_2CH_2O)_n\overset{O}{\overset{\|}{C}}CH_2CH(SO_3M)CO_2M$$

wherein n=1 to 20; and M is as defined above.

Sarcosinates are generally indicated by the formula RCON($CH_3$)$CH_2CO_2M$, wherein R ranges from $C_8$ to $C_{20}$ alkyl and M is a solubilizing cation.

Taurates are generally identified by formula $$R^2CONR^3CH_2CH_2SO_3M$$

wherein $R^2$ ranges from $C_8$-$C_{20}$ alkyl, $R^3$ ranges from $C_1$-$C_4$ alkyl and M is a solubilizing cation.

Another class of anionics are carboxylates such as follows:

$$R-(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5-15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application.

Another surfactant which may be used are $C_8$ to $C_{22}$ neutralized fatty acids (soap). Preferably, the soap used are straight chain, saturated $C_{12}$ to $C_{18}$ neutralized fatty acids.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

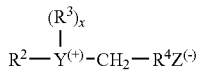

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxy-pentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

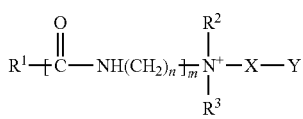

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $-CO_2-$ or $-SO_3-$

Suitable amphoteric detergents within the above general formula include simple betaines of formula:

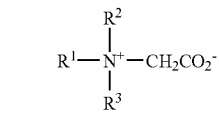

and amido betaines of formula:

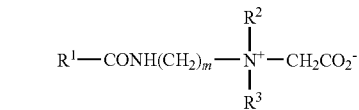

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

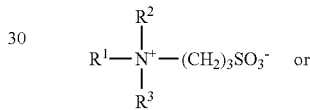

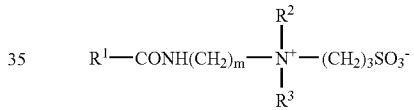

where m is 2 or 3, or variants of these in which $-(CH_2)_3 SO^-_3$ is replaced by

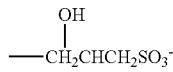

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic surfactant, when used, generally comprises 0% to 25%, preferably 0.1 to 20% by weight, more preferably 5% to 15% of the composition.

In addition to one or more anionic and optional amphoteric and/or zwitterionic, the surfactant system may optionally comprise a nonionic surfactant.

Nonionic Surfactants

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula

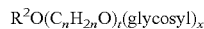
$$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Structurant Benefit Agent Premix

The benefit agent portion of the structured benefit agent may be any of the benefit agents described previously in the section relating to the benefit agent.

Similarly, the crystalline structurant may be any one of the materials described above.

The premix/delivery vehicle is also as described above.

As indicated earlier, the premix should be made separately and it preferably, although not necessarily, may be in a pourable or flowable state (viscosity is lower than 250 Pa-s, more preferably lower than 200 Pa-s, most preferably lower than 150 Pa-s) before adding to the final carrying composition (e.g. liquid composition).

When used in the composition, the structured benefit agent will permit benefit agent deposition of greater than about 5% greater than if the benefit agent had not been structured. In one embodiment, benefit agent is oil and deposition is greater than 60 μg/cm², preferably greater than 75 μg/cm², more preferably greater than 100 μg/cm², and this deposition is not dependent on large droplet size of the structured benefit agent.

Dispersion Stabilizers

Another optional, although preferred, element of the invention is an emulsion stabilizer (found in, for example, liquid aqueous phase). The dispersion stabilizer is intended to provide adequate storage stability to the composition (i.e., so the benefit agent delivery vehicle is stable in the composition). The structured composition otherwise may be prone to separate under the action of gravity (creaming or sedimentation depending upon its density). The structured composition of the invention may also be prone to sticking together and coalescing.

The most effective dispersion stabilizers are those that can provide an adequate structure to the liquid, e.g., aqueous phase to immobilize the droplets thus preventing both gravitational separation and collision with other droplets. However, if the dispersion is too stable, the droplets of structured composition are inhibited from coming into proximity with the skin and thus effectively depositing. Therefore, the most effective dispersion stabilizers provided have excellent stability in the container but lose their effectiveness in immobilizing the structured benefit agent when they are applied to wet skin.

Aqueous dispersion stabilizers useful in the instant invention can be organic, inorganic or polymeric stabilizers. Specifically, the compositions comprise 0.1 to 10% by wt. of an organic, inorganic or polymeric stabilizer which should provide physical stability of the large structured oil droplets, in the surfactant composition at 40° C. for over four weeks.

Inorganic dispersion stabilizers suitable for the invention includes, but are not limited to clays, and silicas. Examples of clays include smectite clay selected from the group consisting of bentonite and hectorite and mixtures thereof. Synthetic hectorite (laponite) clay used in conjunction with an electrolyte salt capable of causing the clay to thicken (alkali and alkaline earth salts such as halides, ammonium salts and sulfates) particularly useful. Bentonite is a colloidal aluminum clay sulfate. Examples of silica include amorphous silica selected from the group consisting of fumed silica and precipitated silica and mixtures thereof.

Organic dispersion stabilizers are defined here as organic molecules that have a molecular weight generally lower than 1000 Daltons and form a network in the aqueous phase that immobilizes the dispersed structured oil phase. This network is comprised either of amorphous solids, crystals, or liquid crystalline phase. Suitable organic dispersion stabilizers for the instant invention are well know in the art and include, but are not limited to any of several types of long chain acyl derivatives or mixtures thereof. Included are the glycol mono- di- and triesters having about 14 to about 22 carbon atoms. Preferred glycol esters include the ethylene glycol mono- and distearates, glyceryl stearates, palm oil glyceride, tripalmitin, tristearin and mixtures thereof.

Another example of organic dispersion stabilizer are alkanolamides having from about 14 to about 22 carbon atoms. Preferred alkanolamides are stearic monoethanolamide, stearic diethanolamide stearic monoisopropanolamide, stearic monoethanolamide stearate and mixtures thereof.

Still another class of useful dispersion stabilizer is long chain fatty acid esters such as stearyl stearate, stearyl palmitate, palmityl palmitate, trihydroxystearylglycerol and tristearylglycerol.

Another type of organic dispersion stabilizers is the so-called emulsifying waxes such as mixtures of cetostearyl alcohol with polysorbate 60, cetomacriogol 1000, cetrimide; a mixture of glycerol monostearate with a stearic soap, and partially neutralized stearic acid (to form a stearate gel).

Still another example of a suitable dispersion stabilizing agent is long chain amine oxides having from about 14 to about 22 carbon atoms. Preferred amine oxides are hexadecyldimethylamine oxide and octadecyldimethylamide oxide.

Example of a suitable polymeric dispersion stabilizing agents useful in the present invention include: carbohydrate gums such as cellulose gum, microcrystalline cellulose, cellulose gel, hydroxyethyl cellulose, hydroxypropyl cellulose, sodium carboxymethylcellulose, hydroxymethyl carboxymethyl cellulose, carrageenan, hydroxymethyl carboxypropyl cellulose, methyl cellulose, ethyl cellulose, guar gum (including cationic guar gum), gum karaya, gum tragacanth, gum arabic, gum acacia, gum agar, xanthan gum and mixtures thereof. Preferred carbohydrate gums are the cellulose gums and xanthan gum.

An especially preferred type of polymeric dispersion stabilizer agent includes acrylate containing homo and copolymers. Examples include the crosslinked poly acrylates sold by B.F. Goodrich under the CARBOPOL trade name; the hydrophobically modified cross linked polyacrylates sold by B.F. Goodrich under the PEMULEN trade name; and the alkali swellable acrylic latex polymers sold by Rohm and Haas under the ARYSOL or ACULYN trade names.

The above dispersion stabilizers can be used alone or in mixtures and may be present in an amount from about 0.1 wt. % to about 10 wt. % of the composition.

Other Ingredients

In addition, the non-bar, preferably liquid compositions of the invention may include optional ingredients as follows:

Perfume, which may be the combination of several fragrances, may be selected on the basis of the ability of the fragrances to be incorporated into the benefit agent delivery vehicle to provide enhanced fragrance delivery/benefit(s). However, as noted, perfume may also comprise a separate benefit agent which may be entrapped in a network formed by different structured benefit agent or may be added separately to the composition and not as part of the premix.

Organic solvents, such as ethanol; auxiliary thickeners, such as carboxymethylcellulose, magnesium aluminum silicate, hydroxyethylcellulose, methylcellulose, carbopols, glucamides, or Antil® from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and Vitamin A, C & E or their derivatives may be used advantageously in amounts of about 0.01% or higher if appropriate.

Polyethylene glycols which may be used include:

| | | |
|---|---|---|
| Polyox | WSR-205 | PEG 14M, |
| Polyox | WSR-N-60K | PEG 45M, or |
| Polyox | WSR-N-750 | PEG 7M. |

Thickeners which may be used include Amerchol Polymer HM 1500 (Nonoxynyl Hydroethyl Cellulose); Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt).

Another optional ingredient which may be added are the deflocculating polymers such as are taught in U.S. Pat. No. 5,147,576 to Montague, hereby incorporated by reference.

Another ingredient which may be included are exfoliants such as polyoxyethylene beads, walnut sheets and apricot seeds Another preferred ingredient is a crystallization suppressant or control agent which is used to suppress individual or mixtures of sunscreen ingredients from crystallizing out of solution. This may lead to reduced deposition. These suppression agents include, for example, organic esters such as $C_{10}$-$C_{24}$, preferably $C_{12}$-$C_{15}$ alkyl benzoate among others. Other examples include Bernel PCM from Bernel, and Elefac 205 from Bernel. Specific sunscreen(s) are more resistant to crystallization than others, e.g., butyl octyl salicylate.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

Protocol

Ingredients Used

Sodium lauryl ether sulfate (SLES) was Steol CS330 from Stepan Co. (Northfield, Ill.).

Cocamidopropyl betaine (CAPB) was Tego Betaine F50 from Goldschmidt Chemical Corp. (Hopewell, Va.).

Guar hydroxypropyl trimonium chloride was Jaguar C-13-S (Rhodia USA, Cranbury, N.J.).

Refined sunflower seed oil was supplied by Welch, Holme and Clark Co., Inc. (Newark, N.J.).

The petrolatum was white petrolatum from Penreco (Karns City, Pa.). The waxes are commercially available from many manufacturers and were directly added to the formulations without further modification.

The commercially available AquaPel 15L from ExxonMobil Chemical is a linear butadiene-isoprene copolymer ($M_w$ 15,000).

Equipment Processing

Small batches of liquid cleanser prototypes were mixed using an overhead stirrer equipped with a high-efficiency paddle. Formulations were prepared in 250 ml stainless steel beakers which were placed in a thermally-controlled water bath (±1.0° C.).

Preparation of Wax-Structured Benefit Agent

Structured (e.g., wax structured) benefit agent premixes (delivery vehicles) were prepared at temperatures at or just above the melting points of the wax structurant or other mixtures of benefit agent and structuring component. Typically, the structuring material was weighed into a 100 ml stainless steel beaker and then the appropriate amount of benefit agent (e.g., sunflower seed oil) was added based on the formulation specifications. The components were then heated by placing the beaker in a thermally-controlled water bath to melt the structuring material (e.g., wax). The molten structured oil was stirred with a stainless steel spatula until uniformly mixed and maintained at the elevated temperature until use (usually no more than 5 min).

Preparation of Liquid Prototype Samples

Liquid cleanser formulations were prepared under similar processing conditions except for differences in mixing temperatures as necessary due to the varying melting temperatures of the structurants. Formulations were prepared in 250 ml stainless steel beakers immersed in a thermally-controlled water bath. First the SLES and CAPB along with additional water were added together and mixed at 100 to 150 rpm for 5 min using an overhead stirrer. Mixing was continued until homogeneous while the temperature was raised to that of the wax-oil premix. Just prior to addition of the oil phase, the mixing speed was increased to 250 rpm. The molten wax-oil premix was then poured into the stirring surfactant mixture and stirred (about 20 minutes) while maintaining the elevated temperature. When mixing was completed, the finished product was removed from the temperature bath and allowed to cool to room temperature without further stirring.

In some examples Jaguar C13S polymer was included in the formulation, which was added after the structuring material—benefit agents (e.g., wax-oil) addition. A premix of Jaguar polymer was prepared as 10% alkaline slurry by dispersing Jaguar C13S powder in 0.1. N sodium hydroxide solution. After addition of the polymer pre-mix, mixing of the formulation was continued for 10 min after which time an appropriate amount of 1N HCl was added to bring the pH of the formulation to pH 6-7. The formulation was stirred for the remaining 20 min and preparation proceeded as described in previous paragraph.

Silicone Rubber Surface Preparation (Silflo)

Silflo silicone rubber material (Flexico Developments, England) was used as received. Silflo replica surfaces for deposition trials were prepared with surface roughness to approximate the skin surface roughness. About 5 ml of Silflo material was squeezed from the stock bottle onto wax paper. After the addition of 2-3 drops of catalyst (supplied with the Silflo) the liquid material will thicken while mixing with a stainless steel spatula (about 30 seconds). A piece of 100 grit sandpaper was cut to 4×4 cm square and taped to a surface to leave approximately 2.5×2.5 cm exposed. The thickened material. was spread evenly over the sandpaper and allowed to dry (about 10 min). Once set, the solid Silflo replica was separated by peeling away the sandpaper and covering the exposed adhesive side of the tape with new pieces of tape. The replica surface was a negative of the sandpaper surface and thus is textured. The 100 grit was chosen to approximate the surface roughness of skin.

Sunflower Seed Oil Deposition Protocol

The amount of sunflower seed oil that deposits from the wax structured oil formulations was assessed on the Silflo replica surfaces. Newly prepared samples of formulations were tested in triplicate by applying product to the Silflo surface, rubbing in the product, rinsing and then extracting any oil remaining bound to the surface. In practice, 8.6 mg of product was applied per square centimeter of surface. After addition of one drop of tap water, the product was rubbed on the surface with one finger for 15 seconds (approximately 20 circular rubs). The surface was then rinsed with tap water maintained at 37° C. and a flow rate of 13-14 ml/sec, holding the sample 5 cm away from the tap at an angle of 45°. After rinse, the sample was blotted once with a towel and allowed to air dry for 15 min. The Silflo replica was then cut from the tape border with a razor blade and placed into a 20 ml glass vial with 10 g of hexanes. After mixing with an automatic "wrist action" shaker for 15 min, the Silflo replica was removed from the vial. For analysis of oil content, the extraction solvent was transferred to 1 ml glass vials.

Sunflower Seed Oil Deposition Analysis by Thin Layer Chromatography (TLC)

Analysis of oil concentration in the hexanes extracts was performed using thin layer chromatography (TLC). Samples were spotted onto TLC plates using an automatic TLC spotter (CAMAG Automatic TLC Sampler 4, CAMAG, Switzerland). Along with the sample extracts, six standard solutions of sunflower seed oil in hexanes were also spotted on each plate. Standards were prepared at concentrations ranging from 125 to 450 µg/g. TLC plates were cleaned before use by soaking first in methanol and then isopropanol for 15 min each and then dried overnight. After spotting, plates were placed in a glass TLC chamber containing 100 ml of developing solution (70% hexane, 29% ethyl ether, 1% acetic acid). When the solution had traveled ¾ of the plate height, the plate was removed and air dried overnight. After drying, the TLC plates were immersed in staining solution (aqueous solution containing 10% cupric sulfate, 8% phosphoric acid). After blotting excess staining solution from the plates, they were heated for 30 min on a hotplate set at 165° C. For measurement of the deposited oil, the stained plates, now having charred spots representing the deposited oil extracted from the Silflo surfaces, were digitally scanned using a GS-700 Imaging Densitometer (Bio-Rad Laboratories, Hercules, Calif.). Using the scanning software, the intensity of the sample spots was calculated based on a standard curve generated for the 6 standards applied to the plate. From these apparent intensity values, the concentration of sunflower oil in the extracts was calculated.

Droplet Size Measurement

Droplet size was measured from images captured of the oil droplets in the formulations. Microscopic images were taken from samples of the body wash prototypes by placing a small amount (<0.1 ml) onto a glass slide. The sample was gently spread on the slide following placement of a cover slip. Samples were examined at 100× magnification using an optical microscope (Axioplan Model, Carl Zeiss, Inc., Thornwood, N.Y.). The microscope was equipped with a video camera, image processor and video monitor. The camera was connected to a personal computer and images were digitally captured using appropriate software. Using the imaging software, (structured) oil droplets were measured individually. At least 100 droplets were measured for each sample.

Viscosity Shear Profile Measurement

The Rheometric Scientific ARES controlled strain rheometer (SR-5, Rheometric Scientific, Piscataway, N.J.) was used to determine shear profiles of structured benefit agents used herein. The rheometer was set up with paralled plates 25 mm in diameter typically with 200 to 500 µm gaps between the top and bottom plates. Test temperature were 37° C.

Programmed steady shear rate sweeps were performed where the shear rates were logarithmically varied from 0.1 to 1000 seconds$^{-1}$, with 5 points recorded per decade. The shear scan typically takes 5 minutes to complete. The output is viscosity as a function of shear rate.

Yield Stress Measurement

The yield stress values of the structured benefit agents were measured using a Rheometric Scientific Stress Controlled Rheometer model SR-5 (Rheometric Scientific, Piscataway, N.J.). Stress ramp tests were performed on samples in stress ranges from 0.2 to 12000 Pa using either a 25 mm or 40 mm cone and plate fixture. Samples of the structured benefit agent to be tested were loaded between the fixture (top plate) and bottom plate. Using the RSI Orchestrator software supplied with the instrument, tests were conducted by incrementing the applied stress from 0.2 Pa to user defined final stress value. The user also sets testing time typically at 15 minutes. Tests are completed when the sample yields (flows), which is noted by a sharp decrease in sample viscosity as observed as the software plots the experimental data as the test is conducted. Yield stress values were determined from linear plots of the viscosity versus strain. The first data point after the peak of the curve is the yield value. Alternatively, lines can be fit to the linear portions of the curve before and after the peak. The intersection of the line will give the yield value. Yield stress can also be determined from semi-logarithmic plots of the viscosity (Pa-s) against stress (Pa). The yield value is the first data point for stress after the linear portion of the curve at lower stress values. The yield stress values here are to be understood as a critical yield stress value or the value of the stress where the material begins to flow.

Example 1 and 2 and Comparatives A to C

This example is to highlight the advantage of structuring the benefit agent and of the order of addition of structurant and benefit agent.

Shower formulations were prepared having various compositions. A liquid cleanser composition without benefit agent (sunflower seed oil) being structured (Comparative A) was prepared at room temperature by mixing 20% w/w of sunflower seed oil with 80% aqueous surfactant phase (comprising water and surfactants) using an overhead mechanical mixer equipped with a high efficiency stirrer and stirring at 250 rpm.

Comparative A composition is set forth below:

| Comparative A (Control, Skin Cleanser Base) | |
|---|---|
| Component | % wt. |
| Sodium Laureth Sulphate | 13.0 |
| Cocamidopropyl Betaine | 7.0 |
| Sunflower Seed Oil (unstructured) | 20.0 |
| Di Water | To 100.0 |
| Ph = 6.0-7.0 | |

Examples 1 and 2 were prepared by mixing 25% w/w of a structured benefit agent oil (comprising 5% w/w of a structurant such as petrolatum or ultraflex or amber wax; and 20% w/w sunflower seed oil) to the aqueous surfactant phase. For these formulations, the structured oil was prepared by addition of the structurant to the sunflower seed oil, heating the mixture to a temperature above the melting point of the structurant and mixing until uniform. The molten structured oil was only then combined with (e.g., added to) the aqueous surfactant phase which was maintained at the same temperature as the structured oil. After mixing for 15 minutes, the formulation was cooled to room temperature. The structurant must be, and was, added to the oil phase prior to dispersion of the structured oil phase into the aqueous surfactant phase.

An example of the composition of the invention is set forth below as Example 1.

Example 1 (Invention, Cleanser+5% Petrolatum)

| Component | % Wt. |
|---|---|
| Sodium Laureth Sulphate | 13.0 |
| Cocamidopropyl Betaine | 7.0 |
| Petrolatum (Structurant) | 5.0 |
| Sunflower Seed Oil | 20.0 |
| Di Water | To 100.0 |

Example 2 (Invention, Cleanser+5% microcrystalline wax) was prepared in the same way as Example 1 except the structurant was microcrystalline wax. That is, the example comprises the same formulation as Example 1, except 5.0% petrolatum is replaced by 5.0% ultraflex® amber wax.

Comparative B (Comparative, Cleanser+5% petrolatum) comprises the same formulation as Example 1, including use of 5% petrolatum structurant. It differs from Example 1 only in that the 5% petrolatum and the sunflower seed oil were added separately to the surfactants.

Comparative C (Comparative, Cleanser+5% microcrystalline wax) comprises the same formulation as Example 2 and differs only in that the 5 wt. % ultraflex amber wax and sunflower seed oil were added separately to the surfactants.

Table 1 below sets forth the deposition results for each of the compositions:

Sunflower Seed Oil Deposition from Formulations with Structured Oils

TABLE 1

| Formulation | Deposition, μg/cm$^2$ |
|---|---|
| Comparative A (no structurant) | 0 |
| Example 1 | 158 |
| Comparative B (separate addition of oil and structurant) | 34 |
| Example 2 | 980 |
| Comparative C (separate addition) | 49 |

As seen from Table 1, the importance of the order of addition of the components to create the structured oil is demonstrated by comparing oil deposition from Examples 1 and 2 with formulations prepared from the same components but differing processing conditions. Comparatives B and C were prepared by the separate addition of structurant and sunflower seed oil to the aqueous surfactant phase. For these formulations, 5% w/w of structurant, 20% w/w sunflower seed oil and 75% of aqueous surfactant phase were heated in separate vessels to the same temperature which is above the melting point of the structurant. The sunflower seed oil was added to the aqueous surfactant phase and mixed with an overhead stirrer as described above. The structurant was then added separately to the mixture and the entire formulation was mixed for 15 minutes. After mixing, the formulation was cooled to room temperature.

As seen clearly, Comparative B & C (separate addition) have far less deposition.

Example 3 to 5 and Comparative D

A liquid cleanser with the composition shown in Comparative A plus the addition of an oil phase structurant was used to prepare Examples 3-5 and Comparative D Example 3 (Invention, Cleanser+5% paraffin wax) comprises the same formulation as Example 1 except that is uses 5% paraffin as structurant instead of 5% petrolatum. It is prepared as per the invention, i.e., structurant and oil mixed before addition to surfactant phase.

Example 4 (Invention, Cleanser+5% animal wax) comprises same formulation as Example 1 except that it uses 5 wt. % beeswax as structurant instead of 5% by wt. petrolatum. Again, structurant and oil are combined before combining with surfactant phase.

Example 5 (Invention, Cleanser+2.5% petrolatum+2.5% microcrystalline wax) comprise same formulation as Example 1 except it uses 2.5 wt. % petrolatum and 2.5 wt. % ultraflex amber wax (microcrystalline wax) instead of 5% by wt. petrolatum. Again structurant and oil are combined separately from combination with surfactant phase.

The following comparative was also prepared.

Comparative D (Comparative, Cleanser+10% polymer thickener, which is AquaPel 15, a linear copolymer of butadiene/isoprene) uses a non-crystalline linear polymer used as a benefit agent (oil) structurant.

| Component | % Wt. |
| --- | --- |
| Sodium Laureth Sulphate | 13.0 |
| Cocamidopropyl Betaine | 7.0 |
| AquaPel 15L (copolymer of butadiene/isoprene) | 10.0 |
| Sunflower Seed Oil | 15.0 |
| Di Water | To 100.0 |

Sunflower Seed Oil Deposition from Formulations with Structured Oils

TABLE 2

| Formulation | Deposition, µg/cm² |
| --- | --- |
| Comparative A (Sunflower Oil only)* | 0 |
| Example 2 (ultraflex amber wax)* | 980 |
| Example 3 (paraffin wax) | 649 |
| Example 4 (beeswax) | 245 |
| Example 5 (petrolatum + ultraflex wax) | 865 |
| Comparative D (AquaPel 15L) | 51 |

*From previous Table 1

As seen in the example only crystalline wax structurants (2-5) yield sunflower seed oil deposition of 60 µg/cm² or greater. Comparative D, using a non crystalline material, fails to yield these results.

Examples 6-10

In order to show that structuring works with variety of crystalline waxes at small droplet sizes averaging 4.9-6.2 µm diameter) applicants prepared the following examples in accordance with the process of the invention (i.e., benefit agent sunflower seed oil and structurant were first combined)

Example 6 (Invention, Cleanser+5% microcrystalline wax)
95 wt % liquid cleanser of Comparative A
5 wt. % Victory amber wax Example 7 (Invention, Cleanser+5% microcrystalline wax)
95 wt % liquid cleanser of Comparative A
5 wt. % Multiwax ML-445

Example 8 (Invention, Cleanser+5% microcrystalline wax)
95 wt % liquid cleanser of Comparative A
5 wt. % Multiwax 180-M Example 9 (Invention, Cleanser+5% microcrystalline wax)
95 wt % liquid cleanser of Comparative A 5 wt. % Multiwax W-835

Example 10 (Invention, Cleanser+2.5% microcrystalline wax)
97.5 wt % liquid cleanser of Comparative A
2.5 wt. % Mekon white Structured benefit agent droplet size and deposition results are set forth in Table 3 below:

Sunflower Seed Oil Deposition from Formulations with Structured Oils

TABLE 3

| Formulation | Average Droplet Diameter, µm | Deposition, µg/cm² |
| --- | --- | --- |
| Example 6 (Victory amber wax) | 6.2 | 876 |
| Example 7 (Multiwax ML-445) | 6.2 | 852 |
| Example 8 (Multiwax 180-M) | 4.9 | 893 |
| Example 9 (MultiwaxW-835) | 5.9 | 793 |
| Example 10 (Mekon white) | 4.9 | 309 |

As seen from Table 3, sunflower seed oil deposition was excellent over wide range of waxes, and with average droplet sizes much lower than that suggested for best deposition of hydrophobic benefit agent by U.S. Pat. No. 6,066,608, which suggests that droplets have average diameter larger than 200 µm; U.S. Pat. No. 5,854,293, which suggests droplets larger than 500 µm, or U.S. Pat. No. 5,661,189, which suggests droplets from 50-500 µm.

Examples 11-19

In order to show that benefit agent oils can be structured using varying amounts of structurants (e.g., 0.5% to 16.0%) and that level of deposition can be manipulated by amount of structurant, applicants prepared the following examples Example 11 (Invention, Cleanser+0.5% microcrystalline wax)
99.5 wt % liquid cleanser of Comparative A
0.5 wt. % Ultraflex amber wax Example 12 (Invention, Cleanser+1.0% microcrystalline wax)
99.0 wt % liquid cleanser of Comparative A
1.0 wt. % Ultraflex amber wax Example 13 (Invention, Cleanser+2.0% microcrystalline wax)
98.0 wt % liquid cleanser of Comparative A
2.0 wt. % Ultraflex amber wax Example 14 (Invention, Cleanser+4.0% microcrystalline wax)
96.0 wt % liquid cleanser of Comparative A
4.0 wt. % Ultraflex amber wax
Example 15 (Invention, Cleanser+6.0% microcrystalline wax)
94.0 wt % liquid cleanser of Comparative A
6.0 wt. % Ultraflex amber wax
Example 16 (Invention, Cleanser+8.0% microcrystalline wax)
92.0 wt % liquid cleanser of Comparative A
8.0 wt. % Ultraflex amber wax
Example 17 (Invention, Cleanser+10.0% microcrystalline wax)
90.0 wt % liquid cleanser of Comparative A
10.0 wt. % Ultraflex amber wax
Example 18 (Invention, Cleanser+12.0% microcrystalline wax)
88.0 wt % liquid cleanser of Comparative A
12.0 wt. % Ultraflex amber wax
Example 19 (Invention, Cleanser+16.0% microcrystalline wax)
84.0 wt % liquid cleanser of Comparative A
16.0 wt. % Ultraflex amber wax Deposition results for the various compositions are set forth below:

Sunflower Seed Oil Deposition from Formulations with Structured Oils

TABLE 5

| Example | Deposition, $\mu g/cm^2$ |
| --- | --- |
| 11 (0.5% Ultraflex amber wax) | 65 |
| 12 (1% Ultraflex amber wax) | 213 |
| 13 (2% Ultraflex amber wax) | 320 |
| 14 (4% Ultraflex amber wax) | 727 |
| 2 (5% Ultraflex amber wax) | 980 |
| 15 (6% Ultraflex amber wax | 1022 |
| 16 (8% Ultraflex amber wax) | 1178 |
| 17 (10% Ultraflex amber wax) | 1328 |
| 18 (12% Ultraflex amber wax) | 1080 |
| 19 (16% Ultraflex amber wax) | 1076 |

As seen from Table 5, small or large amounts of structurant can be used. The level of structurant can be used to control deposition (e.g., increasing the amount of structurant can increase the level of deposition as seen, for example, in Table 5).

The wax content is measured as percent of overall composition. That is, for example, Example 12 combines 1% microcrystalline wax with 20% sunflower seed oil in a premix which, when in molten state, is then combined with the rest of the composition (of Comparative A).

Examples 20-21, Comparative E

In order to show that deposition will occur with or without a further aid to deposition (i.e., cationic polymer), applicants made the following examples:
Example 20 (Invention, Cleanser+5.0% microcrystalline wax+1.0% polymer)
94 wt % liquid cleanser of Comparative A
5 wt. % Ultraflex amber wax
1 wt. % Jaguar polymer
Example 21 (Invention, Cleanser+5.0% microcrystalline wax+1.0% polymer)
94 wt % liquid cleanser of Comparative A
5 wt. % Victory amber wax
1 wt. % Jaguar polymer
Comparative E (Cleanser+1.0% polymer)
99 wt % liquid cleanser of Comparative A
1 wt. % Jaguar polymer
Results of deposition are set forth in Table 6 below:

Sunflower Seed Oil Deposition from Formulations with Structured Oils

TABLE 6

| Example | Deposition, $\mu g/cm^2$ |
| --- | --- |
| Example 2 (5% ultraflex amber wax)* | 980 |
| Example 20 (5% ultraflex amber wax, 1% JaguarC13s) | 473 |
| Example 6 (5% victory amber wax)** | 876 |
| Example 21 (5% victory amber wax, 1% Jaguar C13s) | 388 |
| Comparative A (no benefit agent structurant) | 0 |
| Comparative E (no benefit agent structurant, 1% Jaguar C13s) | 44 |

*From Table 1
**From Table 3

As seen from results in Table 6, deposition occurs even without use of cationic polymer deposition aid.

The invention claimed is:
1. Non-bar, personal product composition comprising
(1) 1% to 99% by wt. of a surfactant material selected from the group consisting of anionic, nonionic, amphoteric, cationic surfactants and mixtures thereof; and
(2) a structured benefit agent delivery vehicle composition comprising droplets having an average droplet diameter below 10 μm and wherein said droplets consist essentially of:
(a) 50.0 to 99.9% by wt. of structured benefit agent composition comprising comprises one or more hydrophobic benefit agents or mixtures thereof; and
(b) 50.0 to 0.1% of said benefit agent composition comprises structuring material forming a three-dimensional supporting network in the benefit agent and which material is selected from the group consisting of crystalline structurants selected from the group consisting of natural or synthetic crystalline waxes;
wherein said material of (2)(b) is a natural crystalline wax selected from the group consisting of petroleum based waxes selected from the group consisting of paraffin waxes; animal waxes, and mixtures thereof;
wherein the crystal in said structuring material has an aspect ratio defined by A/B>1, the length A being understood as the longer of the two dimensions when considering length and width, B;
wherein, when said structured benefit agent is separately formed and separately combined with a surfactant containing carrying composition in which the structured benefit agent will be used to deliver benefit agent to substrate there will be provided at least a 5% increase in deposition of benefit agent to said substrate relative to deposition of the same benefit agent not structured; or not being in the presence of a structured benefit agent in the final composition;
wherein said separately formed structured benefit agent(s) is molten, semi-molten or solid at the time of combination with the carrying composition.

2. A composition according to claim 1 wherein there will be provided an increase in deposition of at least 10%.

3. A composition according to claim 1, wherein said benefit agent in said structured benefit agent delivery vehicle composition is selected from the group consisting of silicone oils, fats and oils, waxes, hydrophobic plant extracts, hydrocarbons, higher fatty acids, higher alcohols, esters, essential oils, lipids, vitamins, sunscreens, phospholipids, particles, anti-aging agents, wrinkle-reducing agents, skin-whitening agents, anti-acne agents, sebum-reducing agents, perfumes and mixtures thereof.

4. A composition according to claim 3, wherein said benefit agent is sunflower seed oil.

5. A composition according to claim 1, wherein said structured benefit agent composition is formed by combining benefit agent and structurant at temperatures above the melting point of the structurant to form a molten solution prior to cooling or to combining said molten solution with said carrying composition.

6. A composition according to claim 1, wherein the structured benefit agent, at the time of adding to the carrying composition, has a viscosity no higher than about 250 Pa-s.

7. A composition according to claim 1 comprising 1 to 75% surfactant.

8. A composition according to claim 1, wherein there are one or more additional benefit agents entrapped in a network formed by the delivery vehicle composition (2).

9. A composition according to claim 1, comprising a benefit agent or benefit agents separate from structured benefit agent vehicle composition (2).

* * * * *